United States Patent [19]

Tomita et al.

[11] 4,320,199
[45] Mar. 16, 1982

[54] FERMENTATION PROCESS FOR PRODUCING NOCARDICINS A AND B

[75] Inventors: Koji Tomita, Kawasaki; Hiroshi Tsukiura, Mitaka; Hiroshi Kawaguchi, Tokyo, all of Japan

[73] Assignee: Bristol-Myers Company, New York, N.Y.

[21] Appl. No.: 203,778

[22] Filed: Nov. 3, 1980

[51] Int. Cl.³ .......................... C12P 17/10; C12N 1/20
[52] U.S. Cl. .................................... 435/121; 435/253; 435/822
[58] Field of Search .................. 435/121, 253, 822

[56] References Cited

U.S. PATENT DOCUMENTS 3,923,977  12/1975  Aoki et al. .......................... 424/118
4,212,944   7/1980  Celmer et al. ...................... 435/121

OTHER PUBLICATIONS

Aokai et al., 15th Interscience Conference on Antimicrobial Agents (Abstract 97), 1975.
Aokai et al., Journal of Antibiotics, vol. 29, pp. 492–500 (1976).
Hashimoto et al., Journal American Chemical Society, vol. 98, pp. 3023–3025 (1976).
Kurita et al., Journal of Antibiotics, vol. 29, pp. 1243–1245 (1976).
Derwent Abstract 02700c of Japanese Patent Publication 54-151,196.
Derwent Abstract 35223c of Japanese Patent Publication 55-45,327.

*Primary Examiner*—Lionel M. Shapiro
*Attorney, Agent, or Firm*—Richard R. Lloyd

[57] ABSTRACT

The known antibiotic, nocardicin, is produced by submerged aerobic cultivation of *Microtetraspora caesia* sp. nov. ATCC 31724 or 31725.

5 Claims, No Drawings

FERMENTATION PROCESS FOR PRODUCING NOCARDICINS A AND B

SUMMARY OF THE INVENTION

This invention relates to a process for the preparation of the known antibiotic nocardicin by cultivating a strain of *Microtetraspora caesia* sp. nov. having the identifying characteristics of ATCC Nos. 31724 or 31725 under submerged aerobic conditions in an aqueous medium until a substantial amount of nocardicin is produced in the culture medium and, optionally, recovering nocardicin from the culture medium. As with prior art procedures, this process provides a mixture of nocardicin A (the major component) and nocardicin B (the minor component) which, if desired, may be readily separated by known procedures.

BACKGROUND AND PRIOR ART (A) Nocardicin was first reported by H. Aoki et al. at the 15th Interscience Conference on Antimicrobial Agents & Chemotherapy (Abstract 97) in 1975. It was then called by the code number FR-1923 and was an antibiotic of unknown structure (although known to contain a β-lactam ring) produced by cultivation of *Nocardia uniformis* var. *tsuyamanensis* ATCC 21806.

(B) U.S. Pat. No. 3,923,977 discloses and claims Antibiotic FR-1923 (then of unknown structure but now known to be nocamycin), and the process for its preparation by fermenting *Nocardia uniformis* var. *tsuyamanensis* ATCC 21806.

(C) H. Aoki et al., J. Antibiotics, 29, 492–500 (1976), in a follow-up publication to that described above, redesignate FR-1923 as nocardicin A, give its structure, and describe its isolation and characterization. They also mention other unidentified minor components in the fermentation broth.

(D) M. Hashimoto et al., J. Am. Chem. Soc., 98, 3023–5 (1976), report the structures of nocardicins A and B produced by *Nocardia uniformis* var. *tsuyamanensis* ATCC 21806. The compounds are stereoisomers at the oxime function; nocardicin A is the compound with the oxime and acylamino moieties in a syn relationship while nocardicin B has these moieties in a trans relationship.

(E) M. Kurita et al., J. Antibiotics, 29, 1243–5 (1976), describe the isolation and characterization of nocardicin B from *Nocardia uniformis* subsp. *tsuyamanensis* ATCC 21806.

(F) Japanese Patent Publication No. 54-151,196 (Derwent 02700C) discloses the preparation of nocardicin A by culturing a new basophile strain of Streptomyces designated *Streptomyces alcalophilus* ATCC 31393.

(G) Japanese Patent Publication No. 55-45327 (Derwent 35223C) discloses the preparation of nocardicins A and B by culturing a strain of *Nocardia* sp. No. C-14509 (FERM-P 4642).

(H) U.S. Pat. No. 4,212,944 discloses and claims a process for producing nocardicin A by fermenting *Nocardiopsis atra* Huang sp. nov. ATCC 31511.

DETAILED DESCRIPTION

The known antibiotic nocardicin having the structure

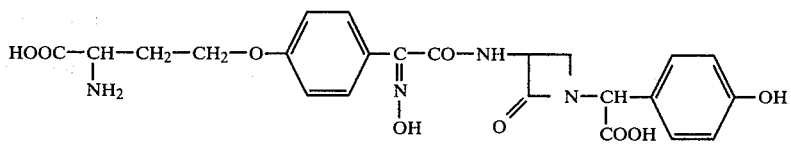

is produced by fermentation of certain new species of the genus Microtetraspora under submerged aerobic conditions in an aqueous culture medium containing assimilable sources of carbon and nitrogen.

THE MICROORGANISM

In the course of screening for β-lactam antibiotics, two unusual actinomycetes strains, Nos. G432-4 and G434-6, which produced nocardicin were isolated from soil samples collected in India. Both strains grow well on natural media or chemically defined organic media at temperatures between 20° C. and 50° C.

Strain No. G432-4 bears thick aerial mycelium on which short spore chains are produced. The spore-chains contain 2 to 6 spores in a chain and develop into a thick mass on agglomerated sporophores. The aerial mass color is pale blue or gray-greenish blue. Two types of spore-enveloping vesicles, as well as motile spores with single polar flagellum, are formed in the substrate mycelium. A dark grayish-green pigment, slightly diffusible into agar, is produced in most agar media. Unlike Strain No. G432-4, Strain No. G434-6 produces no or scant aerial mycelium and no greenish pigment. It forms two spore-enveloping vesicles and flagellated spores in the thick substrate mycelium as observed with strain G432-4.

The two strains possess, as diagnostic cell wall components, meso-diaminopimelic acid, glucose and a small amount of mannose and rhamnose. Nocardomycolic acid is absent in the vegetative mycelium.

As the results of comparative studies with several genera of the Actinomycetales, Strains Nos. G432-4 and G434-6 were determined to be a new species of genus Microtetraspora. The new species name *Microtetraspora caesia* is proposed for strains G432-4 and G434-6 in view of the bluish-gray colored aerial mycelium. Cultures of strains G432-4 and G434-6 have been deposited in the American Type Culture Collection, Washington, D.C., and added to its permanent collection of microorganisms as ATCC Nos. 31724 and 31725, respectively.

MATERIALS AND METHODS

Microorganisms used for comparative studies include the following: *Actinomadura madurae* (Vincent) Lechevalier and Lechevalier 1968; *Micropolyspora angiospora* Zhukova, Tsyganov and Morozov 1967 KCC A-0109; *Micropolyspora caesia* Kalakoutskii 1964 KCC A-0098; *Micropolyspora faeni* Cross, Maciver and Lacey 1968 KAA A-0099; *Nocardia corallina* (Bergey et al.) Waksman and Henrici 1948; *Nocardia lutea* Castellani and Chalmers 1919; *Nocardia uniformis* subsp. *tsuyamanensis* Aoki et al. 1967 ATCC 21806; *Nocardiopsis das-*

*sonvillei* (Brocq-Rousseu) Meyer 1976 ATCC 23218; *Microtetraspora viridis* Nonomura and Ohara 1971 KCC A-0112; and *Saccharopolyspora hirsuta* Lacey and Goodfellow 1975 KCC A-0170.

References used for cultural and physiological studies are: (1) Shirline, E. B. and D. Gottlieb: Methods for characterization of Streptomyces species, Int. J. Syst. Bacteriol., 16, 313–340 (1966). (2) Waksman, S. A.: The Actinomycetes, Vol. 2, (1961). (3) Luedemann, G. M.: *Micromonospora purpureochromogenes* (Waksman and Curtis 1916) comb. nov. (subjective synonym: *Micromonospora fusca* Jensen 1932), Int. J. Syst. Bacteriol., 21, 240–247 (1971).

References used for chemical analyses of the cell wall are: (1) Yamaguchi, T.: Comparison of the cell-wall composition of morphologically distinct actinomycetes, J. Bacteriol., 89, 444–453 (1965). (2) Lechevalier, M. P. and H Lechevalier: Chemical methods as criteria for the separation of nocardiae from other actinomycetes, Biology of the Actinomycetes and Related Organisms, 11, 78–92 (1976).

References used for taxonomic descriptions are: (1) Bergey's Manual of Determinative Bacteriology, 8th ed. (edited by R. E. Buchanan and N. E. Gibbons) 599–861, 1974. (2) Actinomycetales: characteristics and practical importance (edited by G. Sykes and F. A. Skinner). Society for Applied Bacteriology Symposium Series No. 2, 11–91, 1973.

MORPHOLOGY

The hyphae of substrate mycelium, 0.4 to 0.8 $\mu$m in diameter, develop on an agar surface or penetrate into agar and branch dichotomously. Partial fragmentation of the substrate mycelium which produces short filaments is observed after 3 to 4 weeks on solid media. This is more markedly observed with the aerial mycelium-lacking strain, G434-6. The aerial hyphae of strain G432-4 are long and moderately branched. Short spore-chains are formed only on the aerial mycelium. Two to six, and occasionally eight, spores are born in a chain, and branched spore-chains are often formed. The spore-chains are borne either directly at the side of the hyphae or on monopodially branched short sporophores. Sporulation develops from monopodial branching of sporophores and basipetal budding in the hyphal sheath. The sporophores which agglomerate along the hyphal axis develop into thick masses of spores with culture age.

The spores are spherical or oval in shape, 0.7–1.0 by 0.7–1.6 $\mu$m in size, and have a smooth surface. Occasionally, aerial hyphal tips are segmented like a spore-chain, and asporogenic spiralling hyphae are singly formed in the aerial mycelium. In the substrate mycelium, spherical or oval translucent capsules (vesicles) which envelop single spores or straight chains of two to six spores are found. In addition, irregularly or tightly coiled spore-chains are occasionally observed. The above-described structures are formed in nutritionally rich media such as malt-yeast or Bennett's agar after 3 to 4 weeks' incubation at 28° C. Oval or banana-shaped motile spores are formed in the aqueous suspension of the mycelial mass. The motile spores have single long polar flagellum and form germ-tubes after incubation.

CULTURAL CHARACTERISTICS

Strains G432-4 and G434-6 are obligately aerobic, and grow moderately in the range of 20° C. to 50° C. Strain G432-4 grows even at 55° C. but strain G434-6 does not. The colonies on yeast-malt agar are circular and thick, have radial or irregular wrinkles, and become 3 to 5 mm in diameter after incubation at 37° C. for a week.

Strain G432-4 forms abundant aerial mycelium, bears pale blue or gray-greenish blue spore-chain masses on Czapek's agar, yeast-malt agar, oat meal agar, glycerolasparagine agar and tyrosine agar, and produces weakly diffusible green pigment in most agar media. Strain G434-6 does not produce aerial mycelium, spores or pigment in ordinary agar media (ISP Medium Nos. 2, 4, 5 and 6 and Bennett's agar), but forms scant to some aerial mycelia and spores in Czapek's agar and ISP Medium Nos. 3 and 7. The cultural characteristics of strains G432-4 and G434-6 are summarized in Table 1.

TABLE 1

Cultural Characteristics

| | * | Strain No. G432-4 | Strain No. G434-6 | *Micropolyspora caesia* KCC A-0098 | *Nocardia uniformis* subsp. *tsuyamanensis* ATCC 21806 |
| --- | --- | --- | --- | --- | --- |
| Czapek's agar: Sucrose nitrate agar | G | restricted | scant | none | abundant |
| | R | colorless | light yellowish-brown | | vivid orange |
| | A | dull bluish-green | poor, pale blue | | none |
| | D | none | none | | none |
| Tryptone-yeast extract broth: | | sedimented, not turbid, pigment not produced | sedimented, membranous, not turbid, pigment not produced | sedimented, not turbid, produced light green diffusible pigment | floccose, pigment not produced |
| Yeast extract-malt extract agar | G | abundant | abundant | moderate | moderate |
| | R | deep orange | light yellowish-brown | dark grayish-green | strong yellowish-orange |
| | A | poor, white later grayed greenish-blue | none | scant, light grey | none |
| | D | none | none | none | none |
| Oat meal agar: ISP No. 3 medium | G | moderate | abundant | scant | moderate |
| | R | light yellowish-brown | dull yellow | | strong yellowish-orange |
| | A | poor, white later light grayish-blue | none or scant, white later grayish-leaf | | none |
| | D | pale yellowish-pink | none | | none |
| Inorganic salts- | G | moderate | poor | scant | moderate |

TABLE 1-continued

Cultural Characteristics

| | * | | Strain No. G432-4 | Strain No. G434-6 | Micropolyspora caesia KCC A-0098 | Nocardia uniformis subsp. tsuyamanensis ATCC 21806 |
|---|---|---|---|---|---|---|
| starch agar: | | R | light orange | colorless | | yellowish-orange |
| ISP No. 4 medium | | A | lately formed, grayish-blue | none | | none |
| | | D | light orange | none | | none |
| Glycerol- | | G | scant | poor | scant | scant |
| asparagine agar: | | R | colorless | colorless | colorless | colorless |
| ISP No. 5 medium | | A | poor, pale sky | none | none | none |
| | | D | none | none | none | none |
| Peptone-yeast ex- | | G | scant | none or trace | moderate | restricted |
| tract iron agar: | | R | colorless | | colorless or olive | colorless |
| ISP No. 6 medium | | A | none | | none | none |
| | | D | none | none | none | none |
| Tyrosine agar: | | G | restricted | poor | scant | poor |
| ISP No. 7 medium | | R | light yellowish-brown | light yellowish-brown | grayish-blue | vivid yellowish |
| | | A | moderate, light grayish green | scant, white later pale green | none | none |
| | | D | none | none | none | yellowish-pink |
| Glucose-ammonium | | G | moderate | restricted | poor | restricted |
| salts agar | | R | colorless | strong yellowish-orange | dark grayish-olive | light yellowish-brown |
| | | A | none or scant | none | none | none |
| | | D | strong reddish-orange | none | none | none |
| Bennett's agar | | G | abundant | moderate | moderate | moderate |
| | | R | light yellowish-brown | colorless | colorless to grayish-olive | yellowish-orange |
| | | A | poor, white later light grayish-blue | none | none | none |
| | | D | none | none | none | none |

Incubation for observation: 1 to 3 weeks at 28° C.
*G = Growth,
R = Reverse color,
A = Aerial mycelium,
D = Diffusible pigment

PHYSIOLOGICAL CHARACTERISTICS

Strains G432-4 and G434-6 are resistant to the action of lysozyme. Their growth is restricted in the presence of 3% NaCl and completely inhibited at 5%. Nitrate is not reduced to nitrite in peptone broth or glucose Czapek's broth. Gelatin is liquefied by strain G432-4 but not by strain G434-6. Milk is peptonized completely by strain G432-4 but only partially by strain G434-6. Hydrogen sulfide is produced from cysteine. Melanoid pigments are not produced in ISP Medium Nos. 1, 6 and 7. In Luedemann's potato plug test, growth is not inhibited at pH 5.7. Acid is not produced from glucose, fructose or glycerol. The physiological characteristics of strains G432-4 and G434-6 are shown in Table 2.

TABLE 2

Physiological Reactions

| Test | Response | Method and Medium |
|---|---|---|
| Nitrite from nitrate | Negative | Inorganic medium: Czapek's glucose nitrate broth |
| Nitrite from nitrate | Negative | Organic medium: 0.5% yeast extract, 1.0% glucose, 0.5% KNO$_3$, 0.1% CaCO$_3$ |
| Resistance to sodium chloride | Restricted growth at 3%, no growth at 5% | Basal medium: 1% yeast extract, 2% soluble starch, 1.5% agar |
| Resistance to lysozyme | Resistant | Gordon's glycerol broth. Lysozyme at 0.001%. |
| Effect of pH: Potato plug | Normal growth both in acidic and neutral plugs | Leudemann's potato agar |
| acidity Acid from glycerol, fructose & glucose | Negative | Basal medium: 0.1% (NH$_4$)$_2$HPO$_4$, 0.02% KCl, 0.02% MgSO$_4$, 0.2% peptone, 1.5% agar. Indicator: Brom Cresol Purple. |
| Casein hydrolysis in agar medium | Positive | Luedemann's agar medium |
| Reactions in skimmed milk solution | Weakly coagulated and/or peptonized in strain G432-4. No or scant growth in strain G434-6. | |
| Gelatin stab | Liquefied in strain G432-4. Not liquefied in strain G434-6. | |
| H$_2$S production from L-cysteine | Positive | L-cysteine (0.1%) added to tryptone-yeast extract broth (ISP No. 1 medium) plus agar. H$_2$S detected with a paper strip containing 10% aq. lead acetate solution. |
| Hydrolysis of tyrosine | Weakly hydrolyzed | L-asparagine was omitted from the tyrosine agar so as to include L-tyrosine as a sole nitrogen source. |
| Formation of | Negative | Tryptone-yeast extract broth, peptone-yeast |

TABLE 2-continued

Physiological Reactions

| Test | Response | Method and Medium |
|---|---|---|
| melanoid | | iron agar & tyrosine agar. |
| Effect of temperature | Moderate or abundant growth at 20° C. to 50° C. No growth at 10° C. Strain G432-4 grows moderately at 55° C. but not at 60° C. Strain G434-6 does not grow at 55° C. | Yeast extract-malt extract agar. |

The carbon source utilization patterns of strains G432-4 and G434-6 are shown in Table 3. The two strains utilize glycerol, L-arabinose, D-xylose, L-rhamnose, D-glucose, D-galactose, D-fructose, D-mannose, lactose, cellobiose, melibiose, trehalose, starch and D-mannitol for growth. L-sorbose, D-melezitose, dulcitol, inositol and D-sorbitol are not utilized by either strain. In addition, sucrose and raffinose are not utilized by strain G432-4.

TABLE 3

Utilization of Carbon Sources

| Strain No. | G432-4 | G434-6 | Micropolyspora caesia KCC A-0098 | N. uniformis subsp. tsuyamanensis ATCC 21806 | Microtetraspora viridis KCC A-0112 |
|---|---|---|---|---|---|
| Glycerol | + | + | + | + | + |
| D(−)Arabinose | + | + | − | − | − |
| L(+)-Arabinose | + | + | + | + | + |
| D-Xylose | + | + | + | + | + |
| D-Ribose | + | + | + | − | + |
| L-Rhamnose | + | + | − | + | + |
| D-Glucose | + | + | + | + | + |
| D-Galactose | + | + | + | + | + |
| D-Fructose | + | + | + | + | + |
| D-Mannose | + | + | + | + | + |
| L(−)-Sorbose | − | − | − | − | − |
| Sucrose | − | + | − | + | + |
| Lactose | + | + | − | + | + |
| Cellobiose | + | + | + | + | + |
| Melibiose | + | + | − | + | − |
| Trehalose | + | + | − | + | + |
| Raffinose | − | + | − | − | − |
| D(+)-Melezitose | − | − | − | − | − |
| Starch | + | + | + | + | + |
| Dulcitol | − | − | − | − | − |
| Inositol | − | − | − | − | − |
| D-Mannitol | + | + | + | + | + |
| D-Sorbitol | − | − | − | + | − |
| Salicin | + | − | − | − | + |
| Cellulose | − | − | − | − | + |
| Chitin | − | − | − | − | + |
| Keratin | − | − | − | − | + |

Incubation for observation: 2 weeks at 28° C.
Basal medium: Luedemann's medium composed of 0.5% yeast extract, 0.1% CaCO₃ and 1.5% agar

CELL WALL COMPOSITION

As shown in Table 4, the cell wall of strain G434-6 contains meso-diaminopimelic acid and a trace amount of glycine as diagnostic amino acids. The whole cell hydrolyzate contains glucose, mannose and a trace amount of ribose and rhamnose as neutral sugar. Thus, meso-diaminopimelic acid (DAP) is considered to be the sole diagnostic component in the cell wall composition of strain G434-6. Therefore, the cell wall of strain G434-6 can be classified as Type IIIc. The absence of nocardomycolic acids in the lipid fraction of the cell wall of strain G434-6 was indicated according to the method of Mordarska, Mordarski and Goodfellow, J. Gen. Microbiol., 71, 77–86 (1972).

TABLE 4

Chemical Composition of Cell Wall

| Strain No. | G434-6 | Microtetraspora viridis KCC A-0112 | Micropolyspora caesia KCC A-0098 | Micropolyspora angiospora KCC A-0109 | Actinomadura madurae |
|---|---|---|---|---|---|
| Meso-DAP | ++ | ++ | ++ | ++ | ++ |
| LL-DAP | − | − | − | − | − |
| Glycine | TR | − | − | − | − |
| Galactose | − | − | ++ | − | ++ |
| Glucose | ++ | + | − | + | − |
| Mannose | + | − | − | + | TR |
| Madurose | − | TR | − | + | ++ |
| Arabinose | − | − | ++ | − | − |
| Xylose | − | − | − | − | − |
| Ribose | TR | TR | TR | ++ | − |
| Rhamnose | TR | − | TR | TR | − |

TAXONOMY

Strains Nos. G432-4 and G434-6 were compared with six genera of the order Actinomycetales, i.e., Nocardia, Micropolyspora, Microtetraspora, Nocardiopsis, Saccharopolyspora and Actinomadura, which possess spore-chains on aerial mycelium and meso-diaminopimelic acid in the cell wall. Strains G432-4 and G434-6 resemble a few species of the genus Micropolyspora in the formation of greenish-blue masses of short spore chains on aerial mycelium and in the basipetal budding sporulation, but differ from them in the lack of spore chain clusters in substrate mycelium, their resistance to lysozyme, sensitivity to sodium chloride and the absence of arabinose and galactose in the cell wall. The genera Nocardiopsis and Saccharopolyspora bear spores in the entire parts of aerial mycelium. The aerial spores of these genera are formed in such a way that hyphae divide into long segments which subsequently subdivide into smaller fragments of irregular size. On account of these distinct sporulating mechanisms, strains G432-4 and G434-6 are easily distinguished from the genera Nocardiopsis and Saccharopolyspora. In addition, the two new strains differ from the genus Nocardiopsis in their resistance to lysozyme; and differ from the genus Saccharopolyspora in their smooth spore surface, the lack of arabinose in the cell wall, resistance to lysozyme and sensitivity to sodium chloride. Strains G432-4 and G434-6 resemble a few species of the genus Actinomadura which form blue-green aerial mycelium and aerial short spore-chains, but differ from the latter in the basipetal budding type sporulation, the formation of less spores in a chain, spore-chain cluster and the lack of madurose in the whole cell hydrolyzate. The sporogenic species of the genus Nocardia such as *N. mediterranea* or *N. uniformis* subsp. *tsuyamauensis* have some similarities to the present new strains in the formation of short spore-chains, the lack of acid production from glucose, fructose and glycerol, resistance to lysozyme and sensitivity to sodium chloride. However, the basipetal budding, the spherical spores, the distinct spore-chain cluster containing many branched sporophores, the fused chains of one to several spores and the green-blue thick aerial mycelium of strains G432-4 and G434-6 are easily distinguishable from the sporogenic species of Nocardia which bear rod-shaped spores occurring by segmentation in the hyphae and which have the ability to form single spore-chain and rudimental aerial mycelium with white or pale color.

According to the descriptions by Thiemann et al., J. Gen. Microbiol., 50, 295–303 (1968), the genus Microtetraspora (*M. fusca* and *M. glauca*) is characterized by bearing short spore-chains (mostly 4 spores in a chain) only on aerial mycelium, and by having meso-DAP, glycine, lysine, a trace amount of LL-DAP and no diagnostic sugar in the cell wall. Nonomura and Ohara, J. Ferment. Technol., 49, 1–7 (1971) and 49, 887–894 (1971), reported two additional species in the genus Microtetraspora, *M. viridis* and *M. niveoalbida*, which possess only meso-DAP as the diagnostic component of the cell wall. As shown in Table 5, strains G432-4 and G434-6 are closely related to the genus Microtetraspora in the major characteristics including the spore-chain and spore morphology, the mode of sporulation, the responses to lysozyme or sodium chloride, and the cell wall composition. Thus, strains G432-4 and G434-6 were compared with four known species of Microtetraspora. None of the four species grow at 45° C., but strains G432-4 and G434-6 grow at 50° C. The color series of the aerial mass is gray for *M. fusca* and *M. glauca*, green for *M. viridis* and white for *M. niveoalba*, while the aerial mass color of strain G432-4 is placed in the blue series.

TABLE 5

Major Characteristics of Nocardicin-Producing Organisms and Related Genera with Meso-DAP in Cell Wall

| | Strain Nos. G432-4 & G434-6 | Nocardia | Micropolyspora | Microtetraspora | Nocardiopsis | Saccharopolyspora | Actinomadura |
|---|---|---|---|---|---|---|---|
| Aerial mycelium: | | | | | | | |
| Formation | Present; scant to abundant | Absent or rudimental | Present; scant to abundant | Present; scant to abundant | Present; sparse to thick | Present; sparse | Present; scant to abundant |
| Color | Greenish-blue | White | White, yellow, blue, green, gray | White, gray, green | White, yellow, gray | White | All color types |
| Spore-chain | Clusters consisting of single spores, longitudinal pairs of spores and chains of 2 to 8 spores | Short chains (not in cluster) | Clusters consisting of single spores and chains of 2~20 spores | Clusters consisting of chains of several spores (mostly 4 spores) | 10–50 spores in a chain. Hyphae dividing into long segments, subdividing into smaller spores of irregular size. | 10~50 spores in a chain. Each spore in chain often separated by lengths of empty hyphae. | 5~15 spores in a chain |
| Mode of sporulation | Basipetal; budding | Segmentation of hyphae | Basipetal, budding | Basipetal, budding | Segmentation in hyphae | Segmentation in hyphae | Segmentation in hyphae |
| Surface of spore | Smooth | Smooth | Smooth, warty or spiny | Smooth | Smooth | Tufts of long or curved hairs | Smooth, warty or spiny |
| Substrate mycelium: | | | | | | | |
| Degree of fragmentation into rods or coccus | + | +++ | ++ | − | + | + | − |
| Spore-chains in substrate mycelium | Absent | Absent | Present | Absent | Absent | Absent | Absent |
| Special morphology | Two types of spore-bearing vesicles, and motile spore | Fragmentation of substrate mycelium | *M. angiospora* forms translucent capsule, enveloping spores | A species bears segmented hyphae | Zigzag-shaped mycelium at the beginning of aerial sporulation which occurs in total mycelia | Sporulation occurs in total parts of aerial mycelium | Slime-enveloping hooks or closed spirals; pseudo-sporangia |
| Cell wall | | | | | | | |

TABLE 5-continued

Major Characteristics of Nocardicin-Producing Organisms and Related Genera with Meso-DAP in Cell Wall

| | Strain Nos. G432-4 & G434-6 | Nocardia | Micropolyspora | Microtetraspora | Nocardiopsis | Saccharopolyspora | Actinomadura |
|---|---|---|---|---|---|---|---|
| composition: | | | | | | | |
| Diagnostic amino acid & sugar (Type) | Meso-DAP, glucose, mannose | Meso-DAP, arabinose, galactose (IV$_A$) | Meso-DAP, arabinose, galactose (IV$_A$) | Meso-DAP, glucose, traces of glycine, aspartic acid, rhamnose (III$_C$) | Meso-DAP (III$_C$) | Meso-DAP, arabinose, galactose (IV$_A$) | Meso-DAP, madurose (III$_B$) |
| Nocardomycolic acid (LCN-A) | − | + | + | − | − | − | − |
| Resistance to Lysozyme (0.001%) | + | + | − | + | − | − | * |
| NaCl (7%) | − | + | + | − | + | + | − |
| Acid from Glucose, fructose & glycerol | − | + | − | − | − | − | − |

*reported (−) in literature but showed (+) by our test

Strain G434-6 produces two types of vesicles in the substrate mycelium: One is translucent vesicles enveloping one to several spores in a straight line and the other vesicles form irregularly and tightly coiled spore-chain mass. Motile spores with single polar flagellum are also produced in the substrate mycelium. *Micropolyspora angiospora* is reported to have translucent capsule enveloping spores. However, the formation of motile spores has not been reported for any genera of the families Micromonosporaceae and Nocardiaceae (Bergey's Manual, 8th ed., 1974). The formation of fruit vesicle, cartilaginous vesicle and motile flagellated elements (motile isogamates) has been reported for *Streptomyces sindenensis* by Nakazawa, Ann. Rep. Takeda Res. Lab., 25, 24 (1966). Although motile spores are observed capriciously in strain G434-6, the morphological relationship of spore-bearing vesicles or motile elements is *S. sindenensis* and strain G434-6 is not clear. Therefore, the two types of vesicles and the motile spores are not considered to be significant morphological structures to determine a taxon. On the basis of the above-mentioned major characteristics, Strain Nos. G432-4 and G434-6 have been determined to be a new species of the genus Microtetraspora. These two strains have been designated *Microtetraspora caesia* sp. nov.; the type strain is No. G432-4.

Since *Microtetraspora caesia* strains G432-4 and G434-6 are easily mutated naturally or artificially, it is to be understood that the present invention is not limited to these original strains. It is specifically intended to include all nocardicin-producing natural and artificial mutants and variants which can be produced from the described strains by such means as X-radiation, ultraviolet radiation, treatment with nitrogen mustards, phage exposure and the like. As with other microorganisms and antibiotics, it is anticipated that higher production of nocardicin may be achieved by the selection of highly productive strains after single colony selection, by treatment with various mutagens, or by the genetic procedures of recombination, transformation or transduction.

PREPARATION OF NOCARDICIN

Nocardicin is produced by culturing a strain of *Microtetraspora caesia* having the identifying characteristics of strains G432-4 (ATCC 31724) or G434-6 (ATCC 31725) under submerged aerobic conditions in an aqueous nutrient medium. The general procedures used for the cultivation of other actinomycetes are applicable to the cultivation of *Microtetraspora caesia*. The nutrient medium should contain one or more assimilable carbon sources such as glycerol, glucose, fructose, mannose, starch, dextrin, maltose, mannitol, molasses, oils, fats and the like, either in purified or the crude state. The nutrient medium should also contain one or more assimilable nitrogen sources such as, for example, soybean meal, fish meal, malt extract, peptone, yeast extract, distiller's solubles, gluten meal, cornsteep liquor, cottonseed flour, casein, hydrolyzed protein substances, nitrates, ammonium salts, urea and the like. Nutrient inorganic salts such as sodium chloride, potassium phosphate, magnesium sulfate, calcium carbonate and trace amounts of heavy metal salts such as copper, zinc, manganese, iron, and the like, may also be added to the nutrient medium. In the submerged aerated culture, an antifoam such as liquid paraffin, soybean oil, fat or silicone may be added.

The fermentation temperature should be in the range of from about 20° to about 50° (55° in the case of strain G432-4), preferably in the range of from about 25° to about 40°, and most preferably in the range of from about 25° to about 35°. The pH of the fermentation medium should be in the range of from about 5 to about 10, and the preferred range is from about 6 to about 8.5. Ordinarily, optimum production of nocardicin is obtained in from 3 to 7 days, depending on the temperature. When tank fermentation is to be carried out, it is desirable to produce a vegetative inoculum in a nutrient broth by inoculating the broth medium with a slant or soil culture, or a lyophilized culture of the microorganism. After obtaining an active inoculum in this manner, it is transferred aseptically to the fermentation tank medium. The antibiotic activity in the fermentation broth may be determined by a paper disc-agar plate assay using *Pseudomonas aeruginosa* strain Pa-49 as a test organism (which has a specific sensitivity to β-lactam antibiotics) or by known procedures described in the prior art for nocardicin production.

Recovery of nocardicin from the culture medium may be accomplished by procedures previously described in the literature [e.g. in J. Antibiotics, 29, 492–500 and 1243–5 (1976)] or as described in the Examples below. The utility of nocardicin, dosages and methods of administration are described in the literature. See, for example, published U.K. Patent Application No. 2,035,081A which describes its use against various Mycobacterium species such as *Mycobacterium tuberculosis*, *Mycobacterium kansasii*, *Mycobacterium intercellulare* and the like.

EXAMPLE 1

Fermentation of Strain G432-4

A well-grown agar slant culture of Strain G432-4 was used to inoculate 100 ml of liquid vegetative medium in a 500-ml Erlenmeyer flask, which contained the following ingredients: 3% glycerol, 1% Pharmamedia, 1.5% Distiller's soluble (Santory), 1% fish meal and 0.6% $CaCO_3$. The pH of the medium was adjusted to 7.0 before sterilization. The seed culture was incubated at 34° C. for 3 days on a rotary shaker (250 rpm), and 2 ml of the culture was transferred to a 500-ml Erlenmeyer flask containing 100 ml of the same medium. Maximum antibiotic production was obtained after 6 days incubation at 28° C. on a rotary shaker. The broth pH gradually rose with the progress of fermentation to about 8.5 when the antibiotic potency of 150 mcg/ml was reached.

EXAMPLE 2

Isolation and Purification of Nocardicin

A fermentation broth obtained from a large scale cultivation of Strain G432-4 using the same conditions as in Example 1 (4 L, ca. 150 mcg/ml) was filtered with filter aid. The mycelial cake collected was extracted with methanol (1 L×2), and the extract (1.8 L) was concentrated in vacuo to an aqueous solution (300 ml). This aqueous concentrate was combined with the broth filtrate and washed with ethyl acetate (800 ml×2) at pH 8.2. The aqueous layer was separated, concentrated in vacuo and then stirred with activated carbon at pH 4. The carbon was filtered and the active principle was eluted from the carbon by stirring with 80% aqueous acetone (600 ml×2). The active eluate was concentrated in vacuo and lyophilized to give about 7 g of crude material. The solid was dissolved in a small amount of water and applied to a column containing an acid-treated Diaion HP-20 resin (200 ml). The column was washed with water (1 L) and then developed with 30% aqueous methanol (1.6 L). The active fractions were combined, concentrated in vacuo and lyophilized to give 1.5 g of partially purified material. The solid thus obtained was further purified by HP-20 column chromatography. The active aqueous concentrate was adjusted to pH 2.0 and stored in refrigerator to afford a pure preparation of antibiotic Bu-2445 A as a colorless powder (35 mg).

Antibiotic Bu-2445 was readily soluble in alkaline solution, sparingly soluble in methanol and insoluble in common organic solvents. It gave a positive reaction with ninhydrin test but was negative in the Ehrlich and Tollens reactions. The elementary analysis of Bu-2445 A agreed with a formula of $C_{23}H_{24}N_3O_9 \cdot H_2O$. Calc'd: C 53.28, H 5.05, N 10.79. Found: C 53.33, H 4.54, N 10.83.

The ultraviolet spectrum of Bu-2445 A had the following absorption maxima:

| Solvent | $\lambda_{max}$ in nm ($E_{1cm}^{1\%}$) |
|---|---|
| M/15 phosphate buffer at pH 8 | 273(276) |
| N/10 NaOH solution | 245(376) 283(232) |

The infrared spectrum of Bu-2445 A in KBr had characteristic absorptions at 1730, 1650, 1605 and 1520 $cm^{-1}$.

The NMR spectrum of Bu-2445 A exhibited eight low-field proton signals assignable to aromatic protons and nine proton signals corresponding to methylene and methine groups in the 2.0~5.2 ppm region.

The infrared, ultraviolet, and NMR spectra, as well as the elemental analysis for antibiotic Bu-2445 A were typical for those of nocardicins A and B. This was confirmed by thin layer chromatography of antibiotic Bu-2445 A, which showed the presence of two subcomponents ($A_1$ and $A_2$) which (as shown below) were identical to nocadicins A and B respectively.

| | Rf | | | |
|---|---|---|---|---|
| | Bu-2445 A | | Nocardicin | |
| System | $A_1$ | $A_2$ | A | B |
| Cellulose: n-BuOH—HOAc—$H_2O$ (4:1:2) | 0.27 | 0.38 | 0.27 | 0.38 |
| Cellulose: 70% propanol | 0.14 | 0.23 | 0.14 | 0.23 |

EXAMPLE 3

Fermentation of Strain G434-6

Under the same fermentation conditions (media, inoculum size, temperature) as in Example 1, strain G434-6 was used as the producing organism. The maximum antibiotic production of 200 mcg/ml was obtained after 5 days fermentation at 28° C. on a rotary shaker.

EXAMPLE 4

Isolation and Purification of Nocardicin

A fermentation broth obtained from a large scale cultivation of Strain G434-6 using the same conditions as in Example 3 (10 L, ca 200 mcg/ml) was filtered with filter aid. The mycelial cake was extracted with methanol (0.75 L×2) and the extract (1.5 L) was concentrated in vacuo to an aqueous solution. This solution was combined with the broth filtrate and stirred with activated carbon (85 g) at pH 4. The carbon was recovered by filtration and the active principle was eluted from the carbon by stirring with 60% aqueous acetone containing 1% of concentrated $NH_4OH$ (600 ml×3). The active eluate was concentrated in vacuo to 500 ml. This solution was applied to a column of acid treated Diaion HP-20 resin (700 ml). The column was washed with water (2 L) and the activity was then eluted with 8% aqueous methanol (1.2 L). The active fractions were combined, concentrated in vacuo and lyophilized to give 2.3 g of partially purified material. The solid thus obtained was further purified by HP-20 column chromatography. The active aqueous solution was collected, concentrated, adjusted to pH 2 and stored in refrigerator to afford a pure preparation as a colorless powder (80 mg). Infrared, ultraviolet and NMR analysis showed this material to be identical to that produced in Example 2.

We claim:

1. A process for the preparation of a mixture of nocardicins A and B which comprises cultivating a strain of

*Microtetraspora caesia* sp. nov. having the identifying characteristics of ATCC Nos. 31724 or 31725 under submerged aerobic conditions in an aqueous medium containing assimilable sources of carbon and nitrogen at a temperature of from about 20° C. to about 50° C. until a substantial amount of the nocardicin mixture is produced and accumulated in the culture medium.

2. The process of claim 1 which includes the additional step of recovering the nocardicin mixture from the culture medium.

3. The process of claim 1 or 2 wherein the microorganism is *Microtetraspora caesia* ATCC No. 31724 or 31725.

4. The process of claim 3 wherein the cultivation is conducted at a temperature of from about 25° C. to about 35° C.

5. A biologically pure culture of the microorganism *Microtetraspora caesia* ATCC No. 31724 or 31725 capable of producing a mixture of nocardicins A and B upon cultivation in an aqueous nutrient medium containing assimilable sources of carbon and nitrogen.

* * * * *